(12) United States Patent
Grabbert et al.

(10) Patent No.: US 11,614,435 B2
(45) Date of Patent: Mar. 28, 2023

(54) DEVICES AND METHODS FOR IN SITU SOIL ANALYSIS

(71) Applicant: STENON GMBH, Potsdam (DE)

(72) Inventors: Niels Grabbert, Berlin (DE); Dominic Roth, Blieskastel (DE)

(73) Assignee: Stenon GmbH, Potsdam (DE)

( * ) Notice: Subject to any disclaimer, the term of this patent is extended or adjusted under 35 U.S.C. 154(b) by 391 days.

(21) Appl. No.: 17/054,743

(22) PCT Filed: May 8, 2019

(86) PCT No.: PCT/EP2019/061870
§ 371 (c)(1),
(2) Date: Nov. 11, 2020

(87) PCT Pub. No.: WO2019/215257
PCT Pub. Date: Nov. 14, 2019

(65) Prior Publication Data
US 2021/0223226 A1    Jul. 22, 2021

(30) Foreign Application Priority Data
May 11, 2018  (DE) ...................... 10 2018 111 336.6

(51) Int. Cl.
*G01R 33/54*   (2006.01)
*G01N 33/24*   (2006.01)
(Continued)

(52) U.S. Cl.
CPC ............ *G01N 33/24* (2013.01); *G01N 21/31* (2013.01); *G01N 27/043* (2013.01); *G01N 2033/245* (2013.01)

(58) Field of Classification Search
CPC .............. G01R 33/543; G01R 33/5608; G01R 33/4828; G01R 33/3415; G01R 33/283;
(Continued)

(56) References Cited

U.S. PATENT DOCUMENTS 5,621,669 A    4/1997  Bjornsson
5,739,536 A    4/1998  Bucholtz et al.
(Continued)

FOREIGN PATENT DOCUMENTS

CN    106950183 A    7/2017
EP    1203955 A1    5/2002
KR    20160057140 A    5/2016

OTHER PUBLICATIONS

International Search Report for corresponding PCT Application No. PCT/EP2019/061870 dated Dec. 9, 2019.
(Continued)

*Primary Examiner* — Jermele M Hollington
*Assistant Examiner* — Taqi R Nasir
(74) *Attorney, Agent, or Firm* — Wood, Phillips, Katz, Clark & Mortimer

(57) ABSTRACT

The invention relates to the field of soil analysis, in particular the technical analysis of agricultural or horticultural soils. In particular, the invention relates to a sensor device for in situ soil analysis, to a method for in situ soil analysis, and to a device set up for carrying out the soil analysis method, wherein said device, together and in interaction with one or more of said sensor devices, represents a system for in situ soil analysis. The sensor device has a sensor assembly comprising one or more sensors which are configured individually or cumulatively for the simultaneous in situ measurement of at least two of the following soil properties of a soil to be analyzed and for providing corresponding respective measurement data: (a) impedance spectrum, (b) temperature, (c) absorption spectrum NIR-VIS-UV in a spectral range from NIR (near infrared spectral range) to UV
(Continued)

(ultraviolet spectral range), and (d) acidic or basic character, in particular pH value. In this case, the distance between in each case two of the sensors of the sensor assembly, which is defined with respect to the respective measurement variable sensors, does not exceed a value of 10 cm.

27 Claims, 7 Drawing Sheets

(51) Int. Cl.
G01N 21/31 (2006.01)
G01N 27/04 (2006.01)

(58) Field of Classification Search
CPC ........ G01R 33/307; G01R 33/60; G01V 3/32; E21B 49/08; E21B 2049/085; G01N 24/10; G01N 33/24; G01N 21/31; G01N 27/043; G01N 2033/245
See application file for complete search history.

(56) References Cited

U.S. PATENT DOCUMENTS

| | | |
|---|---|---|
| 5,859,536 A | 1/1999 | Stockton |
| 7,944,220 B2 | 5/2011 | Lock |
| 9,285,501 B2 | 3/2016 | Colin et al. |
| 2003/0009286 A1* | 1/2003 | Shibusawa ........... A01B 79/005 |
| | | 702/2 |
| 2015/0216442 A1 | 8/2015 | Lavy et al. |
| 2016/0033437 A1 | 2/2016 | Anjum et al. |
| 2017/0299546 A1 | 10/2017 | Rutz et al. |
| 2018/0085003 A1 | 3/2018 | Goldring et al. |
| 2018/0292339 A1* | 10/2018 | Gunzenhauser ..... G01N 27/045 |

OTHER PUBLICATIONS

International Preliminary Report on Patentability for corresponding PCT Application No. PCT/EP2019/061870.
John M. Dell et al. "MEMS-based Fabry-Perot microspectrometers for agriculture", Proceedings of SPIE, 1000 20th St. Bellingham WA 98225-6705 USA, vol. 7319, Apr. 28, 2009, p. 73190K, DOI: 10.1117/12.819909.

* cited by examiner

DEVICES AND METHODS FOR IN SITU SOIL ANALYSIS

FIELD OF THE INVENTION

The present invention relates to the field of soil analysis, in particular—but without this being a limitation—the technical analysis of soils used for agricultural or horticultural purposes. In particular, the invention relates to a sensor device for in situ soil analysis, a method for in situ soil analysis and a device which is arranged to carry out the soil analysis method, whereby this device, together and in co-operation with one or more of said sensor devices constitutes a system for in situ soil analysis.

BACKGROUND OF THE INVENTION

In the field of soil analysis, laboratory-based methods of analysis are currently mainly used, which are based on the taking one or more samples from a soil to be analyzed, transporting them to a suitable laboratory where they are processed and analyzed. Thereafter, a corresponding analysis report is prepared and sent to a recipient or client. As a rule, the time between the taking of the sample and the notification of the analysis result takes at least several days, but mostly weeks, in particular during times of high demand, such as for example in spring (for Central Europe). In a typical standard laboratory for soil analysis, water content, micro- and macronutrient content, electrical conductivity, soil type, pH value, as well as available and total amounts or concentrations of nitrogen, phosphorus and carbon can be determined by means of standardized laboratory-based analysis methods. A typical soil sample for a farmer includes for example the parameters of soil type, nitrogen, phosphorus, potassium, magnesium, boron, copper, zinc, manganese and iron content, as well as the pH value of the soil and possibly a statement about its requirements as regards lime. Although the methods which are used in such laboratory analyses are very accurate, they cannot be used "in situ", i.e. not without the prior taking of a sample and not on site, on the soil to be analyzed, for example on an area for agricultural or horticultural use, either because the technical equipment which is required for this purpose is not mobile, or because the analysis requires standardized environmental conditions that can only be achieved in a laboratory.

As an alternative to soil analysis in a laboratory, some methods for in situ or semi in situ analysis of soil are already available today. However, the available range of analyses is limited to the analysis of the water content, the pH value, the electrical conductivity and the soil type of the soil from the soil sample. However, other parameters, such as in particular the parameters highly relevant for farmers and horticulturists concerning the content of potassium, magnesium, copper, manganese, zinc, bromine, iron, available phosphorus, humus, as well as the total nitrogen content and the total carbon content cannot be analyzed in situ at present. In addition, on their own, none of the in situ analysis methods known to date enables the measurement results or analysis results to be documented in a manner that is reliable, from a legal point of view, as may be required in many countries as a basis for a verification of legal regulations, such as statutory fertilizer regulations etc.

Known from U.S. Pat. No. 5,621,669 A is a sensor probe for humidity and other properties of bulk material. It includes selection, input, excitation and isolation functions for obtaining signals from a group of sensors, for converting the signals into digital information, for correlating parts of the information and for transmitting the information to one or more external actuators and remote receivers and controllers.

Known from US 2003/0009286 A1 are a device and a method for the acquisition of soil characteristics, which are arranged to effect an efficient detection of high precision data information about the distribution of soil characteristics in an agricultural field, and to manage the data information collectively.

Known from U.S. Pat. No. 9,285,501 B2 is a multi-sensor system for fast in-situ measurement of diffuse reflection from soil, of soil conductivity and of other soil properties in three dimensions.

Known from U.S. Pat. No. 7,944,220 B2 is a moisture content sensor for the measurement of the moisture content of a medium. The sensor includes a probe which injects an electrical signal into the medium. Complex impedance circuitry located between the probe and the electrical signal source enable sensing electronics to generate a signal that indicates the moisture content within the medium based on changes in the permittivity of the medium.

Known from U.S. Pat. No. 5,859,536 A is a sensing device which includes a pair of sensing electrodes which are disposed within a medium, and a circuit connected to the sensing electrodes via impedance matching networks for producing an output signal which varies in response to a capacitive change in the medium. The circuit includes a first circuit portion including the sensing electrodes and a second circuit portion including an oscillator. The first and second circuit portions are tuned to match their impedance to enable a more accurate measurement of the capacitive changes.

Known from CN 106950183 A is a portable device for the detection of soil nutrients based on a spectrum technology.

Known from US 2018/0085003 A1 is a hand held spectrometer which can be used to illuminate an object and to measure one or more spectra. The spectral data of the object can be used to determine one or more attributes of the object. In particular, the spectrometer can be coupled to a database of spectral information that can be used to determine the attributes of the object. The spectrometer system may include a hand held communication device that is coupled to a spectrometer and on which the user can make inputs related to the measured object.

Known from US 2016/0033437 A1 is a remote sensor platform with a low-cost touch sensor which is coupled to capacitive plates for measuring the capacitance of a soil. The sensor platform may also have other sensors to measure other garden parameters, such as for example soil resistance, soil pH value, ambient light, soil or air temperature and air humidity. Based on measurements of the resistance and the capacity of the soil, the moisture content of the soil can be determined.

Known from EP 1 203 955 A1 is a soil measurement method, which uses a soil measuring instrument for measuring properties of a soil. The method comprises an acquisition of measurement data from a soil sensor based on information relating at least to the type of soil at a measurement site and the water content. In order to calculate soil properties, the measurement data which have been collected are entered into a model that is determined on the basis of information which relates to this type of soil and the water content.

BRIEF SUMMARY OF THE INVENTION

Against this background, it is an object of the present invention to provide improved devices and methods for in situ soil analysis. In particular, it is an object of the invention to provide devices and methods for in situ soil analysis, which, compared to solutions known so far, make it possible to analyze additional soil properties and/or to achieve an improved quality of the analysis results.

The solution of this object is achieved according to the teaching of the independent claims. Various embodiments and further developments of the invention are the subject of the dependent claims.

A first aspect of the invention relates to a sensor device for in situ soil analysis.

The sensor device comprises a sensor assembly with one or more sensors which are configured individually or cumulatively for simultaneous in situ measurement of at least two, preferably at least three, or all, of the following soil properties of a soil to be analyzed and for providing corresponding respective measurement data: (a) impedance spectrum, (b) temperature, and (c) absorption spectrum in a spectral range which extends from NIR (near infrared spectral range) to UV (ultraviolet spectral range), NIR-VIS-UV, and optionally (d) acidic or basic character, in particular pH value. The distance between each two sensors of the sensor assembly, defined in relation to their respective measurand transducers, does not exceed a value of 10 cm, preferably 5 cm and particularly preferably 3 cm. In order to measure, in situ, the impedance spectrum, the sensor assembly is configured to measure an alternating current resistance of a portion of soil to be measured, as a function of the frequency of an alternating measuring voltage which is applied to the portion of soil.

In the sense of the invention, the expression "in situ soil analysis" is intended to be understood to mean an analysis of a soil, in particular of a soil in an area which is used for agricultural or horticultural purposes, in which a measurement of desired soil properties is carried out on site on the soil itself, without there being a need to take samples from the soil. In particular, an in situ soil analysis can be performed in such a way that a corresponding sensor device is arranged on or above the soil to be analyzed, or is introduced into it, at least partially, so that the sensing components of the sensor device can measure the relevant property of the soil, whereby the soil, at least substantially, remains unchanged in place. For the purpose of a further soil analysis beyond the mere acquisition of measurement data, an evaluation of the measurement data which have been generated by means of one or more in situ measurements can also be carried out "in situ", i.e. at the location of the measurement, but without this being mandatory. In contrast to this, soil analyses which are based on the fact that a sample is first taken from the soil to be analyzed, which, at the same or a different location, is then subjected to a measurement and, if applicable, a further analysis, are not in situ soil analyses in the sense of the invention.

The expression "simultaneous" in situ measurement of several soil properties is intended to be understood to mean an "in situ" measurement process in which the measurement periods for the measurement of at least two of the soil properties to be measured overlap at least partially. In particular, therefore, measurements of several soil properties which in fact take place exactly simultaneously are also simultaneous measurements in the sense of the invention, as are measurements in which, for example, a first measurement period for the measurement of a first soil property does not exactly coincide with a second measurement period for a second soil property, but there is at least one time interval within which both properties are measured simultaneously. In this context, a measurement period for a soil property is defined as a period of time during which corresponding sensing components are active in order to perform a respective measurement of the soil property itself or of a quantity which is used in order to determine this indirectly.

In the sense of the invention, the expression "impedance spectrum" is intended to be understood to mean a spectrum which represents an alternating current resistance (impedance Z) of a material, in this case of a portion of soil to be measured, as a function of the frequency ($\omega$) of an alternating measuring voltage which is applied to the portion of soil, for example by means of electrodes, which can be done in particular by means of a mathematical function $Z(\omega)$. In this context, the alternating current resistance of a bipolar network element (here the portion of soil) is defined as the ratio of electrical voltage to electrical current.

In the sense of the invention, an absorption spectrum is intended to be understood to mean an electromagnetic spectrum which contains "dark" spectral lines, i.e. incisions in the spectral range, which arise when broadband electromagnetic radiation irradiates or passes through matter and radiation quanta (photons) of certain wavelengths or wavelength ranges are absorbed by the matter. In this context, one or more different absorption mechanisms can occur, mostly dependent on the wavelength. In particular, electronic transitions between different energy levels of atoms, molecules or crystals or other solids (e.g. in the context of luminescence), as well as excitations of other degrees of freedom, in particular of rotational or vibrational degrees of freedom of molecules and in solids, are possible. By means of a comparison of the obtained absorption spectra, in particular reflection spectra, with corresponding reference spectra, qualitative and/or quantitative conclusions can be drawn regarding the material composition of the measured matter.

In the sense of the invention, the expression "measurand transducer" or, for short, "transducer" is intended to be understood to mean a part of a measuring device, i.e. a sensor, which responds directly to a measurand. Thus the transducer is the first element of a measurement chain. In particular, the transducer may—but without this being a limitation—be implemented in the form of one or more electrodes, an optical receiver, or a temperature sensor. The distance between two transducers is to be understood to be the shortest distance between them.

The sensor device according to the first aspect of the invention is characterized by the fact that, on the one hand, it is able to detect at least two different soil properties in a sensor based manner and, at least substantially, in a manner that is non-destructive, which, in addition, are selected in such a way that a clear correlation exists between them, which makes it possible to achieve, by means of data fusion, an increased measurement accuracy from the measurement data obtained by means of measurement, when compared with the individual measurements, and thus an increased quality of the soil analysis. In addition, the measurand transducers of the sensors are concentrated in a very small area (e.g. in an area 100 $cm^2$, preferably 25 $cm^2$, particularly preferably 9 $cm^2$), so that the portion of soil subjected to the measurement can be assumed, in good approximation, to be homogeneous, which is used to further improve the measurement accuracy, in particular with regard to the fact that the correlation between the individual measurement results is strongly dependent on the distance and, as a rule, only allows a significant improvement of the quality of the soil analysis to be achieved by means of data fusion if the distances are small.

In addition, the measurements take place simultaneously, so that time-dependent measurement errors can be minimized. Such a measurement error could otherwise occur, for example, if an impedance measurement led to a local warming of the soil, which would then lead to distorted temperature readings in the case of a subsequent temperature measurement taken at a different time. In addition, the combination of the different measurement methods mentioned above allows soil properties to be achieved by combining the measurement data of the individual measurements, which goes beyond previous possibilities for in situ measurements. Also, a simultaneous measurement reduces the total time required for the measurement process when compared with purely sequential individual measurements.

As there is no need either to take soil samples or to take them to an ex situ laboratory, the results of the soil analysis can be made available in the shortest possible time, in particular also on site, immediately during the course of measurement, so that no significant time delay is necessary until the analysis results are made available.

In the following, preferred embodiments of the sensor device will be described, each of which, as far as this is not expressly excluded or technically impossible, can be combined in any desired manner with one another, as well as with the other aspects of the invention which are described herein.

In some embodiments, the sensor assembly comprises an impedance sensor for in situ detection of an impedance spectrum of the soil to be analyzed. This comprises (i) a first support element; (ii) two conductive tracks which are arranged on the first support element but which are electrically insulated from this and from each other, at least one of which contains an electrically conductive, corrosion resistant polymer or composite material; (iii) and a control device. The control device is configured to apply an AC voltage between the two conductive tracks, to vary its frequency over a predetermined frequency range, and during the course of this, during operation of the sensor device, when this is introduced into the soil to be analyzed in such a way that the conductive tracks are in electrical contact with the soil to be analyzed, to detect an impedance spectrum of the soil to be analyzed in response to the AC voltage applied to it via the conductive tracks and to provide the impedance spectrum in the form of corresponding measurement data. In this way, the sensor device is able to record an impedance spectrum of the soil to be analyzed, with the help of which, in particular, various soil types, soil textures, conductivities, water content, ion concentrations and ion types can be determined.

The particular construction of the conductive tracks on the support element, as well as the particular choice of material for these, enable both a particularly good electrical contact to the surrounding soil to be achieved, as well as a high resistance, in particular resistance against abrasion and corrosion, with respect to the soil and thus a long service life of the sensor device.

The conductive tracks can in particular be wound on the first support element, preferably in such a way that the two conductive tracks run parallel to each other, which is a particularly accurate solution and one which is optimum in terms of the use of space. Here, the term "electrical conductivity" is intended to be understood to mean a physical quantity that indicates how well a substance is able to conduct electrical current. Accordingly, in the sense of the invention, the expression "electrically conductive" is intended to be understood to mean an electrical conductivity which (at 25° C.) is at least 106 S/m, i.e. one which is at least equal to the conductivity of metals.

In some further embodiments, the first support element is electrically conductive, in particular metallically conductive, at least in an area which is covered by the conductive tracks, and the control device is further configured to apply a ground potential to this at least one area during the detection of the impedance spectrum of the soil to be analyzed. In this way, a signal distortion of the recorded impedance spectrum by external electromagnetic coupling can be reduced or even avoided. In this context, the ground potential can in particular be the ground potential (zero potential) of a power supply of the sensor device, for example of a battery used for this purpose.

In some further embodiments, the predetermined frequency range includes the range from 100 Hz to 1 MHz, which makes it possible to determine a spectrum which, due to its width and position within the electromagnetic spectrum, allows particularly good conclusions to be drawn about a large number of different soil properties.

In some further embodiments, the first support element is constructed as a spike which, at least in part, is hollow, for at least partial introduction into the soil to be analyzed. In addition, an insulation layer is applied to the surface of the spike, on which, in turn, the two conductive tracks are arranged, in particular wound. The control device is located in the interior of a hollow portion of the first support element. The construction of the first support element in the form of a spike serves to enable the first support element to be at least partially introduced (stabbed) into the soil to be analyzed, and to thereby bring the conductive tracks, which serve as the measurand transducer of the impedance sensor, into contact with the soil. By means of the insulation, the conductive tracks are electrically decoupled from each other and from the spike, which in particular—as has been described above—can be connected to ground potential. In addition, in the interior of the hollow portion of the first support element, the control device is protected from undesirable influences, in particular from the soil or other parts of the environment, in particular from dust, moisture and substances which cause corrosion.

In some further embodiments, the sensor assembly comprises a temperature sensor for detecting a temperature of the soil to be analyzed, whereby this, together with the impedance sensor, is constructed as an integrated impedance/temperature sensor assembly, which is configured to detect, simultaneously and in situ, an impedance spectrum as well as a temperature of the soil to be analyzed and to make this available respectively in the form of corresponding measurement data. In this way, not only are at least two different measurement quantities determined, which, as has been explained above, makes it possible to broaden a spectrum of soil properties that can be determined, as well as to improve a quality of the analysis, but also a particularly high integration density is made possible, which allows the sensor assembly to be constructed in a particularly space-saving manner.

In particular, the temperature sensor, or parts of it, can, just like the control device, be located in the interior of a hollow portion of the first support element in order to be protected there, like the control device, from undesirable external influences.

The first support element and/or at least one of the conductive tracks can in particular also serve as a temperature measuring probe (i.e. measurand transducer) and, for this purpose, can be connected to the temperature sensor in a heat conducting manner. Preferably, the first support element or, as the case may be, the at least one conductive track is therefore constructed using a material with good thermal conductivity, in particular a metal, such as for example aluminum or a polymer or composite material with good thermal conductivity.

In some embodiments, the temperature sensor is integrated into the control device, for example on a common PCB or a common integrated circuit, which again is advantageous in terms of a high and therefore space-saving integration of the sensor device, in particular also with a view to achieving an arrangement of the measurand transducers of the various sensors of the sensor device that, as far as possible, is optimized in terms of its density.

In some embodiments, the temperature sensor is located in the interior of an electrically conductive portion of the first support element, so that the temperature sensor is at least partially shielded from any electromagnetic interaction generated by the conductive tracks when the AC voltage is applied thereto, as a result of which the measurement accuracy can be increased and undesirable interference effects can be counteracted.

In some embodiments, the sensor assembly comprises an absorption spectrometer assembly for in situ detection of an absorption spectrum of the soil to be analyzed. This comprises at least two MEMS absorption spectrometers (i.e. absorption spectrometers, which are at least partially manufactured by means of MEMS technology, and in particular which contain MEMS components), in particular constructed on the basis of a Fabry-Perot interferometer, the spectral coverage of which differs at least for some portions of the electromagnetic spectrum, whereby an absorption spectrum of the soil to be analyzed can be detected cumulatively by the entirety of the MEMS absorption spectrometers, which absorption spectrum has portions in the NIR range as well as in the VIS range and also in the UV range. In particular, the spectral coverage can extend from the NIR range to the UV range without interruption, and can in particular include the range from 350 nm to 1700 nm to make possible a particularly highly differentiating measurement in a spectral range that, as a rule, is of particular relevance for soil analysis.

In some embodiments, the absorption spectrometer assembly further comprises a movable carrier, in particular a rotatable and/or a translatory displaceable carrier, on which the absorption spectrometers are arranged in such a way that, when the carrier is moved relative to a virtual measuring surface on which the soil to be analyzed comes to rest during the measurement operation of the sensor device, they can spectrometrically measure an area of the soil to be scanned by the absorption spectrometers in order to detect an absorption spectrum which is integrated over the area to be scanned. In this way, results can be achieved which are better usable from a statistics point of view and which are more accurate, whereby the largest possible area of soil can be scanned, ideally at the smallest possible distance. In the case of a rotatable carrier, the absorption spectrum measured can be integrated or averaged, in particular over the angle of rotation of the carrier, and in the case of a translational movement, in particular over the distance of this translational movement. In this way, non-specific characteristics of the soil, for example small stones or branches etc., on average have only a reduced influence, in particular a small influence, on the measurement results obtained, which influence, in addition, can at least largely be eliminated, in particular by means of targeted filtering, for example by means of threshold values.

In some embodiments, at least one source of electromagnetic radiation is also arranged on the movable carrier, which source of electromagnetic radiation is configured, during measurement operation, to irradiate, with electromagnetic radiation, the area of soil to be scanned by the absorption spectrometers during the movement of the carrier relative to the measuring surface in order to generate the absorption spectrum to be measured. In this way, it is possible, on the one hand, to scan an enlarged area of soil due to the movement, but on the other hand to leave the relative positioning of the radiation source to the absorption spectrometers unchanged, which in particular can result in an increased measurement accuracy and can help to reduce or avoid the need for adjustment.

In some embodiments, the absorption spectrometer assembly further comprises a movable shutter device. This is configured to temporarily move a screen into a space defined between the absorption spectrometers and the measuring surface, whereby a calibration reference, such as for example Spectralon in particular, is arranged on the side of the screen which faces towards the absorption spectrometers, for the calibration of at least one, preferably all, of the absorption spectrometers. This enables the sensor device to calibrate itself automatically (e.g. by means of dark current and reference calibration), for example after a certain predetermined number of measurement procedures, in particular also in the context of the in situ soil analysis itself.

In some embodiments, the absorption spectrometer assembly also has an optical system which, in a wavelength range corresponding to the absorption spectrum to be detected, is at least substantially transparent, which optical system is arranged in the space between the absorption spectrometers and the measuring surface, in order to spatially separate these from each other. On its side facing towards the measuring surface, the optical system is provided with a hydrophilic nanocoating, which in particular may also have a higher scratch resistance when compared with the material making up the body of the optical system. With a view to achieving the highest possible scratch resistance, the optical system can in particular also be made of sapphire glass. The spatial separation serves in particular to protect the absorption spectrometers as well as, if applicable, the shutter device against undesired external influences (in particular against dust, moisture, mechanical effects), for example from the soil to be analyzed.

In some embodiments, the sensor assembly comprises a potential measuring assembly for in situ detection of an acidic or basic character, in particular a pH value, of the soil to be analyzed. This comprises the following: (i) a second support element; (ii) an electrolyte/metal reference electrode which is arranged in or on the second support element; (iii) a metal oxide electrode which is arranged on a surface of the second support element, which surface is intended to contact the soil to be analyzed during a measurement operation; (iv) an ion diaphragm which is arranged on the second support element between the metal oxide electrode and the electrolyte/metal reference electrode and which is in contact with the electrolyte/metal reference electrode; (v) a corrosion resistant calibration electrode which is arranged on the surface of the second support element provided for contacting the soil to be analyzed and which corrosion resistant calibration electrode is electrically insulated from the metal oxide electrode; and (vi) a measuring device. The measuring device is configured: (a) in order to determine a current state of the metal oxide electrode, to measure an electrical resistance arising between the calibration electrode and the metal oxide electrode and/or to measure an electrical capacitance arising therebetween when these two electrodes are each in contact with the soil to be analyzed; and (b) in order to determine an acidic or a basic character, in particular a pH value, of the soil to be analyzed, to measure an electrical potential difference arising between the reference electrode and the metal oxide electrode, taking into account a measurement calibration previously determined on the basis of the determined current state of the metal oxide electrode, when these two electrodes are each in contact with the soil to be analyzed.

The measurement of the acidic or basic character of the soil by means of the potential measuring assembly can accordingly be carried out in operation in such a way that, according to the subsidiary feature (b) above, an electrical potential difference arising between the reference electrode and the metal oxide electrode is measured. This potential difference is dependent on the acidic or basic character of the soil which is in contact with the two electrodes during the measurement process, so that the electrical potential difference can be used for the measurement of the acidic or basic character of the soil. The measured potential corresponds, or at least varies in line with, the redox potential between the two electrodes, whereby the associated chemical redox equation is as follows:

$$x\text{Me} + y\text{H}_2\text{O} \leftrightarrow \text{Me}_x\text{O}_y + y2\text{H}^+ + y2e^- \qquad \text{redox}$$

Here, the abbreviation "Me" stands for a metal. The potential difference is thus dependent on the particular electrochemical properties of metal oxide/metal-based sensors, in particular pH sensors, whereby the metal oxide/metal system may in particular be $Sb_2O_3/Sb$, $IrO_2/IR$, $TiO_2/Tl$ or $RuO_2/Ru$. These materials exhibit a direct oxidation or reduction dependence whilst at the same time having a good electrical conductivity in relation to the surrounding hydrogen ion concentration (pH value) in the soil. Their redox potential can thus be correlated to the reference electrode and the acidic or basic character or the pH value of the soil can be determined from this. In addition, the material of the metal oxide electrode is preferably chosen so as to have a good abrasion and impact resistance (with respect to the soil), which is the case with the material systems mentioned above.

The redox potential difference is determined by measuring the ionic currents flowing between the two electrodes through the ion diaphragm, whereby preferably, for the purpose of increased measurability and measurement accuracy, an impedance converter or amplifier is additionally provided in order to convert or to amplify the currents, which possibly are very weak, before they are being measured. The size of the ion diaphragm is also preferably chosen as large as possible in relation to the size of the (second) support element in order to provide the largest possible cross-sectional area for the ion current to flow through the ion diaphragm.

However, as a rule, metal oxides have only limited corrosion resistance to acids or bases, so that when used for soil analysis, metal oxide electrodes often degrade over time, which can lead in particular to a reduction in the layer thickness of the metal oxide electrode with a consequent change in the electrical resistance, thus the current intensity and thus, in turn, the measurement results. Therefore, the measuring device is further configured according to subsidiary feature (a) to determine a current state, in particular a current layer thickness, of the metal oxide electrode by measuring an electrical resistance (or conductivity) arising between the calibration electrode and the metal oxide electrode and/or an electrical capacitance arising therebetween while they are both each in contact with the soil to be analyzed, which then electrically connects both electrodes. The measurement can in particular be performed cyclically.

The conductivity and/or capacity of the soil can, if not known a priori, be determined in particular by means of the impedance sensor of the sensor device mentioned above, so that accordingly the conductivity or the electrical resistance or the capacity of the metal oxide layer can be determined by the measuring device by means of the measurement mentioned above, whereby the conductivity or capacity of the metal oxide electrode correlates directly with the thickness of its metal oxide layer. Thus, the measurement can be recalibrated if necessary, in particular also in a preventive, cyclical manner, by means of the measuring device on the basis of the measurement of the state of the metal oxide electrode, in order to ensure the measurement accuracy even over long periods of time and despite the degradation of the metal oxide.

In some embodiments, the calibration electrode is made of a material that contains an electrically conductive and corrosion resistant polymer and/or composite material. These materials can offer advantages such as in particular a low weight, a high corrosion resistance and a long durability and stability as calibration reference.

In some embodiments, the second support element is constructed as a spike for at least partial introduction into the soil to be analyzed, whereby an insulating layer is applied to the surface of the spike, on which insulating layer the metal oxide electrode, the ion diaphragm, and/or the calibration electrode are arranged. This allows a particularly compact implementation to be achieved. In addition, the electrolyte/metal reference electrode can advantageously be arranged inside the (second) support element, i.e. the spike, and thus be protected against undesired external influences.

In some embodiments, the sensor device further comprises a communication device for the transmission of acquired measurement data to a counterpart which is external with respect to the sensor device, for evaluation. The counterpart can in particular be a separate evaluation device or a remote computing platform, for example in a cloud environment, or a backend server or a distributed computer network. In this way, the further processing of the measurement data for the determination of the final results of the soil analysis can be outsourced from the sensor device, which can be useful in particular if complex, time-consuming calculations are required that can be performed faster or better by central or specialized computing systems than locally by the sensor device itself.

However, in other embodiments it is equally possible to provide the equipment which is necessary for the evaluation of the measurement results in the sensor device itself. But even in this case it may be useful to provide the communication device mentioned above in the sensor device, at least to enable remote updates of software used for the evaluation and/or control of the sensor device.

In some embodiments, the communication device is configured to transmit the measurement data wirelessly by means of communication on the basis of LoRa radio technology and/or NarrowBand Internet of Things, NB-IoT, radio technology. In particular, these technologies are particularly advantageous if the sensor device is intended to be used in locations where other radio data coverage, for example via conventional mobile radio, is missing or is not sufficiently provided. The radio technologies mentioned above allow for wireless data transmission over distances of up to 30 km, which is approximately twice the maximum range (terminal-base station) of conventional mobile radio technologies. The energy consumption is typically very low, so that these technologies can usefully be applied in particular also in mobile, battery-powered devices. In addition, at least the use of LoRa technology is possible on a license-free basis in many countries, which has a corresponding positive effect on the operating costs.

The communication device may in particular also be configured to receive data, in particular data which relates to the outcome of a soil analysis, which data has been determined external to the device, so that corresponding information can be made available to the user in situ, on the sensor device itself, at a suitable man-machine interface, for example a display device or an optical or acoustic output device.

In some embodiments, the sensor device further comprises a secure storage device for storing, protected against unauthorized access, a unique device identification of the sensor device and/or at least a cryptographic key for encrypting measurement data and/or metadata transmitted by means of the communication device. The metadata can in particular—without this being a limitation—represent a location, a point in time and/or a measurement mode of a measurement performed in situ with the sensor device, as well as the device identification or a user identification. In particular, in this way, communication via the communication device, in particular one that is protected against "man-in-the-middle" attacks, as well as a device identity protected against unauthorized modification, can be realized.

In some embodiments, the communication device is further configured to write, into a block chain acting as an external counterpart, measurement data and/or metadata to be transmitted, or to cause another external counterpart to write, into a block chain, the measurement data and/or metadata transmitted to it. These embodiments are advantageous in particular with regard to documentation of the measurement results in a manner that is reliable, from a legal point of view. In addition, these embodiments also allow a protection of communication to be achieved, in particular with regard to a protection against subsequent falsification of the measurement results or soil analysis results obtained.

In some embodiments, the sensor device is configured to carry out an authentication of a user of the sensor device and to allow the transmission of measurement data and/or metadata to an external counterpart only if the authentication has been successful. This measure can also be used to protect the communication and documentation of the measurement results against attacks, in particular with regard to a falsification of the measurement data. Through the use of one or more of the protective measures mentioned above, the requirements for achieving a documentation of the measurement results, which is reliable, from a legal point of view, and which, as the case may be, may be required by law, can thus be met.

In some embodiments, the sensor device further comprises a position determination device for determining a current position of the sensor device and to provide corresponding metadata characterizing the position. In particular, this makes it possible also to provide, together with the measurement data, a location of the measurement by means of corresponding metadata. In addition, a monitoring of the sensor device as regards its spatial position can be implemented in this way, which also provides an additional protection against misuse, in particular misuse by persons who are not authorized.

In some embodiments the sensor device is constructed as a portable unit. This means in particular that the dimensions and the weight of the device allow a human user to carry it easily, without undue problems, for example to a measuring location on agricultural land. Ideally, the dimensions of the sensor device in each direction are therefore a few decimeters maximum, e.g. <50 cm) and the weight is preferably less than 25 kg, ideally less than 10 kg. In this way, the sensor device can be used in a very flexible manner and without the help of vehicles or other maneuvering devices.

A second aspect of the invention relates to a computer implemented method for soil analysis, comprising:
(i) receiving measurement data relating to at least two, preferably at least three, or all of the following soil properties of a soil to be analyzed: (a) impedance spectrum, (b) temperature, (c) absorption spectrum in a spectral range which extends from NIR to UV, NIR-VIS-UV, and optionally (d) acidic or basic character, in particular pH value; and
(ii) determining at least one of the soil properties or at least one soil property derived therefrom on the basis of a combination of the received measurement data by means of data fusion in order to obtain a respective measurement result for the at least one soil property to be determined. With the aid of this method it is thus possible to link the measurement results with respect to the said soil properties within the framework of data fusion, whereby it must again be pointed out that the said soil properties are selected in such a way that, at least for some combinations, there is a correlation between them, which can be used within the framework of the data fusion to obtain more precise or additional results regarding the soil analysis. In particular, the data fusion can be implemented on the basis of fuzzy logic and/or one or more artificial neural networks.

In some embodiments of this, the measurement data are acquired by a sensor device according to the first aspect of the invention, in particular according to one or more of the embodiments thereof described. The method then follows the actual in situ measurement for the acquisition of the measurement data, whereby, for this purpose, the sensor device can in particular, as described above, transmit the measurement data, as well as, if applicable, additional metadata, by means of its communication device via a corresponding communication link to a central or spatially distributed device carrying out the method.

In some embodiments, the method is carried out in at least one central node of a network, in particular a cloud environment or a distributed computer network, which at least one central node, in order to receive the respective measurement data, is configured to be in communication connection with a plurality of sensor devices, in particular according to the first aspect of the invention, for acquiring the respective measurement data. This enables in particular a powerful and variable use of resources for carrying out the method. Also, changes, in particular updates of software used for the execution of the method can accordingly be implemented centrally without having to be distributed to each of the respective sensor devices, so that the overall system can easily be developed further, as well as updated.

A third aspect of the invention relates to a computer program which is configured, when it is run on a processor platform, to carry out the method according to the second aspect of the invention, in particular according to one or more of the described embodiments thereof. The processor platform may contain a single or a plurality of processors and may be implemented in a local, centralized manner, for example in a single computer, or conversely also across a decentralized, distributed computer network. In particular, the processor platform and the computer program may also be present in the sensor device itself in order to enable it to carry out the method.

The computer program may in particular be stored on a non-volatile data carrier. Preferably, this is a data carrier in the form of an optical data carrier or a flash memory module.

This may be advantageous if the computer program as such is meant to be traded independently of a processor platform on which the one or more programs are to be executed. In a different implementation, the computer program may be provided as a file on a data processing unit, in particular on a server, and can be downloaded via a data connection, for example the Internet, or a dedicated data connection, such as a proprietary or a local network. In addition, the computer program may comprise a plurality of interacting, individual program modules.

A fourth aspect of the invention relates to a device for soil analysis, wherein the device is arranged to carry out the method according to the second aspect of the invention, in particular according to one or more of the described embodiments thereof. The device may in particular comprise the said processor platform and thus may, in particular, comprise a single data processing unit, such as a computer, or a decentralized, distributed computer network.

In particular, for some embodiments, the device may itself comprise, for acquiring the measurement data, a sensor device according to the first aspect of the invention, in particular according to one or more of the described embodiments thereof. This is advantageous in particular if the analysis of the measurement data for obtaining further results regarding the soil analysis is to be carried out in situ, i.e. on site at the sensor device itself, which in particular also makes offline operation possible, as well as a determination of such results which is independent of the quality of a communication link to an external processor platform.

The features and advantages explained with respect to the second aspect of the invention similarly apply to the third and fourth aspect of the invention.

Further advantages, features and possible applications of the present invention become clear from the following detailed description in connection with the figures.

DETAILED DESCRIPTION OF THE INVENTION

In the figures, the same reference signs are used throughout for the same or mutually corresponding elements of the invention.

Figure 1:
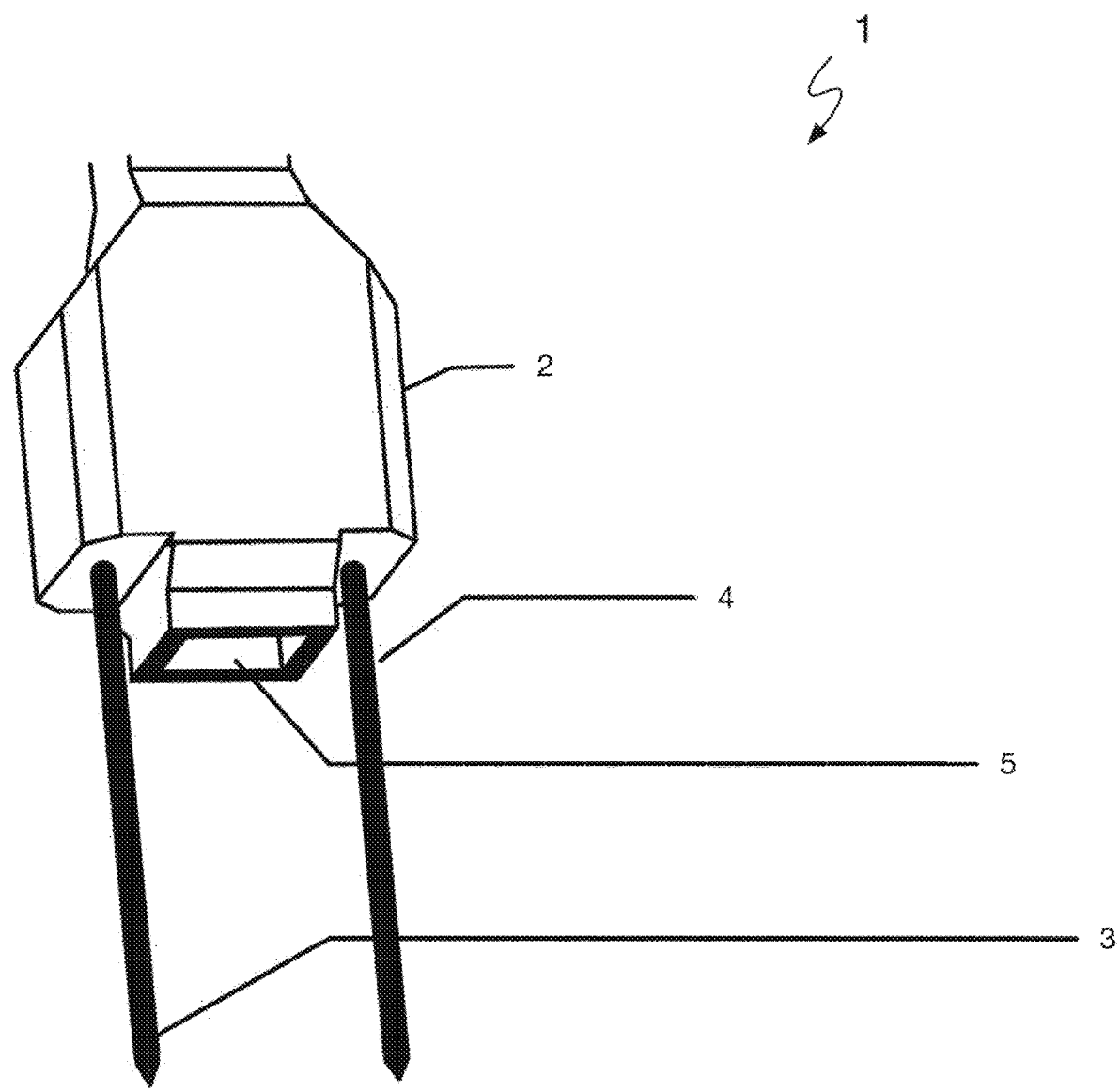
FIG. 1 schematically shows a sensor device according to an embodiment of the invention.

The sensor device 1 shown in FIG. 1 in accordance with an embodiment of the invention is constructed as a module, which in turn comprises several assemblies, in particular sensor assemblies, in a common housing 2. A first one of these assemblies is a combined impedance/temperature sensor assembly 3, which is at least partially constructed in a rod-like or spike-like first support element and which is configured for stabbing into soil to be analyzed. A further one of the assemblies is a potential measuring assembly 4, in particular a pH sensor assembly, which is formed by means of a second support element which, like the first support element, has a rod-like or spike-like shape and is likewise constructed for stabbing into the soil to be analyzed. Between these two assemblies 3 and 4, as well as in the immediate vicinity thereof, an absorption spectrometer assembly 5 is arranged as a further one of the assemblies, which absorption spectrometer assembly 5 has a measuring window which is positioned in such a way that, when the first and the second support element are both stabbed into the soil to be analyzed, it comes to rest on or above the soil. Accordingly, the three sensor assemblies are concentrated in a small area, preferably in a total area of less than 100 $cm^2$, so that the influence of heterogeneities in the soil to be analyzed on the measurement results can be kept low, and in particular reduced to a minimum. The sensor device 1 is constructed as a mobile unit, in particular as a portable unit, preferably weighing less than 25 kg and having a maximum extent of less than 1 m, preferably a maximum of 0.5 m. In addition, the sensor device 1 has an energy supply device (not shown), which can be constructed in particular in the form of a rechargeable, electrochemical energy storage device, such as for example a lithium-ion battery.

The individual assemblies, in particular the sensor assemblies 2, 3 and 4 of the sensor device 1 can also each be constructed as individually removable or exchangeable modules, which in particular makes it possible to generate different sensor configurations in a simple and dynamic way, as well as individually to maintain or to replace the individual sensor assemblies depending on their state of aging or serviceability.

Accordingly, per measurement, the sensor device 1 allows the use of up to four different sensor types and their different measuring principles in order to obtain corresponding measurement data, on the basis of which, with the aid of correlation or data fusion, a determination of soil properties, which goes beyond the direct measurement of soil properties, can be achieved in situ with an accuracy which, in any event, is sufficiently high for many applications. In particular, for example, the impedance of the soil to be measured, the soil temperature, its absorption spectrum in the entire UV-VIS-IR spectral range, as well as its pH value can be measured simultaneously and in the smallest possible space. It is precisely this closely adjacent arrangement of the measurand transducers of the various sensor assemblies 2, 3 and 4 that makes it possible to carry out a successful correlation of the measurement data for the purpose of determining soil properties with the accuracy which is required for typical applications, in particular agrotechnical applications. In addition, the dense arrangement of the measurand transducers also allows ultra-high resolution soil maps to be generated, i.e. soil maps with a grid of less than 100 cm² grid cell area. The simultaneous detection of the different quantities to be measured also makes it possible to represent dynamic and true dependencies between the individual measurement values. In particular, measurement artifacts can thus also be recognized and removed already in situ by means of appropriate evaluation software, for example on the basis of artificial intelligence, in order to further increase the quality of the original measurement results.

Figure 2:
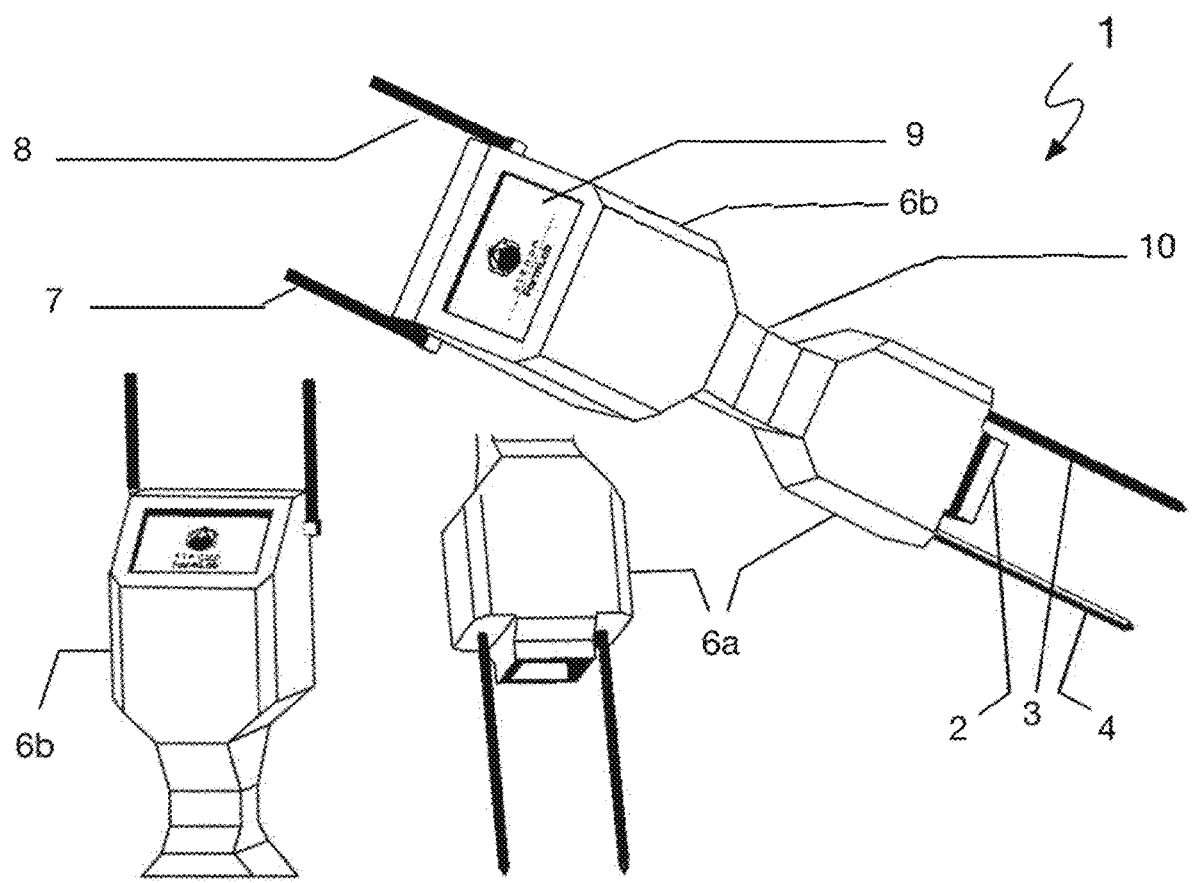
FIG. 2 schematically shows a sensor device constructed in a modular fashion in accordance with a further embodiment of the invention, in which an operating/radio module is provided in addition to a measuring module.

FIG. 2 shows a sensor device 1 constructed in a modular fashion, according to a further embodiment of the invention, which in addition to a sensor module 6a also has an operating/radio module 6b which can be coupled to the sensor module 6a by means of a releasable connection. The two modules 6a and 6b are shown in FIG. 2 on the one hand as separate modules (bottom left) and on the other hand in the connected condition (top right). The housings of the two modules 6a and 6b are preferably constructed in such a way that, when the two modules are connected to each other, a carrying or manipulating handle 10 is formed in the connection region, which carrying or manipulating handle 10 can easily be grasped, in particular reached around, by a human hand, which in particular is also suitable for removing, from the soil, a sensor device 1 that has been stabbed into soil for analysis. As shown in FIG. 2, the handle can be constructed in particular as a reduction of the cross-section of the sensor device 1 in the connection region between the two modules 6a and 6b. The operating/radio module 6b is equipped with a positioning device 7, with the aid of which it is possible to determine the position of the sensor device 1, in particular during a measurement process, and to generate corresponding position data as meta data belonging to the measurement, for example in cooperation with a satellite-based position recognition system such as for example GPS, GALILEO or GLONASS, or with the help of mobile radio-assisted positioning.

In addition, the operating/radio module 6b is equipped with a communication device 8, which in particular can be set up to carry out data communication with an external counterpart by means of mobile radio technology (e.g. 3G, LTE, 5G) or another radio technology, such as LoRa and/or NB-IoT, in particular in order to send measurement data obtained by means of the sensor device 1 to an external data processing center for further evaluation, and in turn, as the case may be, to receive soil analysis results resulting from such evaluation, in order to output them at the sensor device 1 itself at a man-machine interface 9. Such a man-machine interface 9 can be provided in particular in the form of a display device on the sensor device 1, preferably, with regard to a solution that saves as much space as possible, as a control display, which control display enables user inputs as well as the output of information, as is the case, for example, with a touch-sensitive screen.

Figures 3A, 3B:
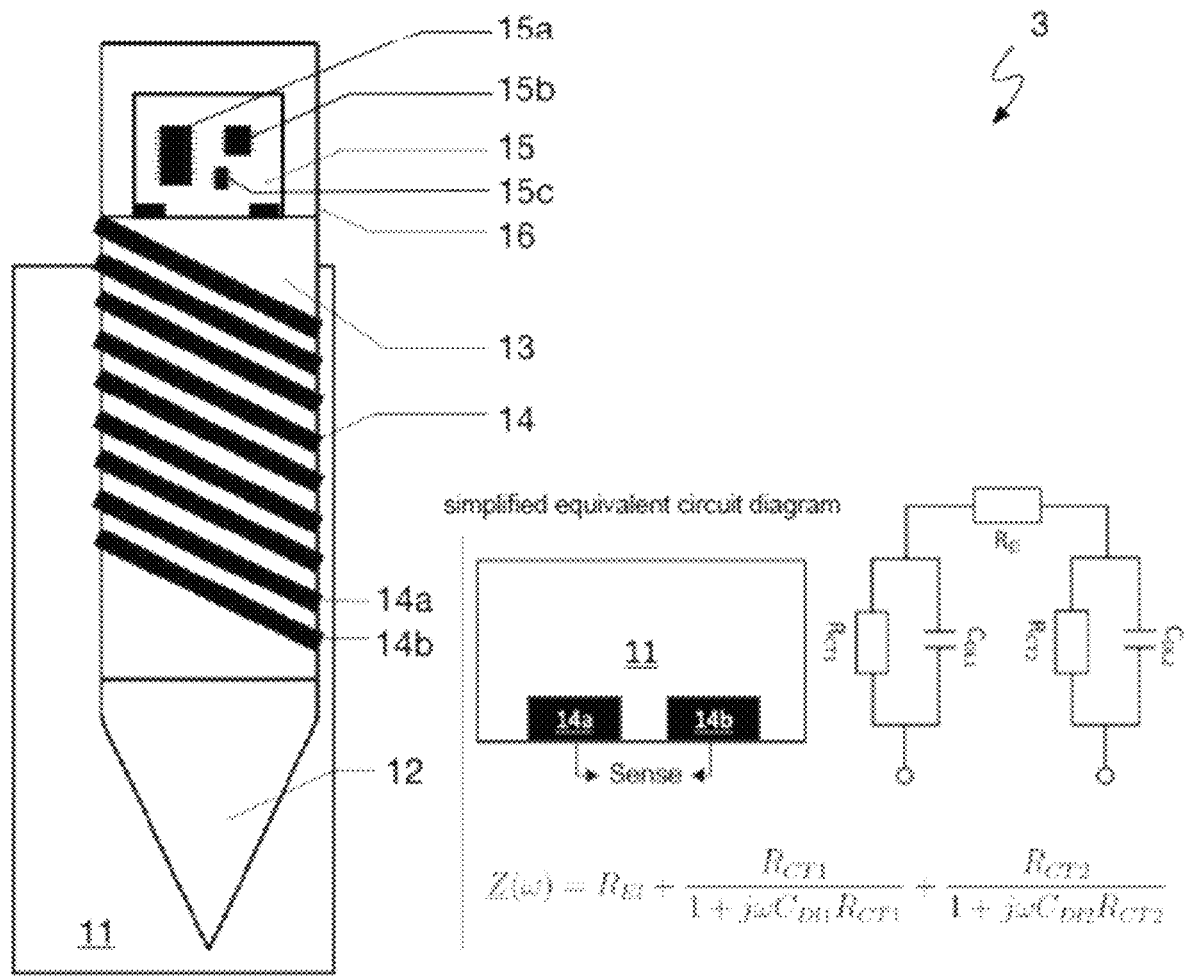
FIG. 3A schematically shows an integrated impedance/temperature sensor assembly for a sensor device according to an embodiment of the invention and FIG. 3B shows a simplified equivalent circuit diagram for this.

FIG. 3A shows an integrated impedance/temperature sensor assembly 3 for a sensor device according to an embodiment of the invention, which integrated impedance/temperature sensor assembly 3 has been stabbed into a soil 11 to be analyzed and which may in particular be provided in a sensor device 1 as shown in FIG. 1 or FIG. 2. To accompany this, FIG. 3B shows a simplified equivalent circuit diagram for the impedance measuring branch of the impedance/temperature sensor assembly 3.

The sensor assembly 3 of FIG. 3A comprises a first support element 12 in the form of a spike, which in particular can be made of metal, preferably of a corrosion resistant metal. The spike may in particular have a substantially cylindrical shape and may be tapered at its end face which is intended for stabbing into the soil, to facilitate the stabbing action. A passivation layer 13 is applied to the first support element 12 on a surface region which typically comes into contact with the surrounding soil in the stabbed-in condition, which passivation layer 13 may in particular contain one or more polymer materials and which acts as an electrical insulator. On the passivation layer 13, two conductive tracks 14 are wound, parallel to each other and without touching each other, around the first support element 12. The two conductive tracks 14 are thus electrically insulated from the support element 12 by means of the passivation layer 13. At its end opposite the tip which can be stabbed into the soil, the impedance/temperature sensor assembly 3 comprises a printed circuit board (PCB) 15 which is arranged in the interior of the support element 12 and which is protected by means of a metal cap 16 (metal housing) located above it, on which printed circuit board (PCB) 15 a control device 15a, a signal preamplifier 15b and a temperature sensor 15c are provided in the form of an integrated circuit or a semiconductor sensor component. The metal cap 16 serves not only for mechanical protection, but also as an electromagnetic shield for the temperature sensor 15c, the control device 15a and the signal preamplifier 15b, which are located in the interior. Aside from serving to control the sensor assembly 3, the control device 15a also serves to measure the impedance and to provide corresponding measurement data, and it is electrically connected to each of the two conductive tracks 14 via the signal preamplifier 15b. The temperature sensor 15c can also be connected to the conductive tracks 14, whereby, in this case, they serve, in addition or alternatively to the first support element 12, as a measurand transducer for the temperature sensor 15c, while in any case they serve as measuring electrodes for the impedance measurement.

Accordingly, the impedance/temperature sensor assembly 3 can be described, as far as its impedance measurement branch is concerned, by means of the simplified equivalent circuit diagram described in FIG. 3B. During the impedance measurement process, a defined alternating measuring voltage is applied by the control device 15a between a first conductive track 14a and the corresponding second conductive track 14b of the two conductive tracks 14. Since during the measurement process the first support element 11 with the conductive tracks 14 located thereon is stabbed into the soil 11 to be analyzed, the two conductive tracks 14a, 14b are in electrical contact with the soil 11 surrounding them then, so that the latter connects the two conductive tracks 14a, 14b in the sense of an electrical resistor $R_{el}$. In the equivalent circuit diagram, the two conductive tracks 14a, 14b respectively have an electrical resistance $R_{CT1}$ and $R_{CT1}$ themselves, as well as a (parasitic) capacitance $C_{DL1}$ and $C_{DL2}$ connected in parallel. By means of the relationship given in FIG. 3B, an impedance spectrum $Z(\omega)$ can accordingly be determined as a function of the frequency $\omega$ of the AC measurement voltage applied. The frequency range used to obtain the impedance spectrum $Z(\omega)$ can be selected in dependence upon the application and typically includes the frequency range from 100 Hz to 1 MHz. The first support element 12 is ideally connected to a ground potential during the impedance measurement process and for this purpose is electrically connected, for example, to the neutral terminal of the power supply of sensor device 1, which counteracts signal distortion of $Z(\omega)$ caused by external electromagnetic coupling.

On the basis of this impedance spectrum $Z(\omega)$ obtained, a distinction with respect to the soil type, the soil texture, the electrical conductivity, the water content, the ion concentration and the ion type can be achieved by further evaluation, in particular by means of dielectric mixture models (for example Bruggeman model, Maxwell Garnett model). Quantitative evaluations are also possible in this way. Simultaneously with the impedance measurement, a temperature measurement can in addition be carried out by means of the temperature sensor, whereby, as already mentioned, the two conductive tracks 14 and/or the first support element 12 can serve as a measurand transducer. Already the impedance/temperature sensor assembly 3 can in some embodiments represent in particular the entirety of the sensors of the sensor device 1, or even the sensor device 1 itself.

Figure 4:
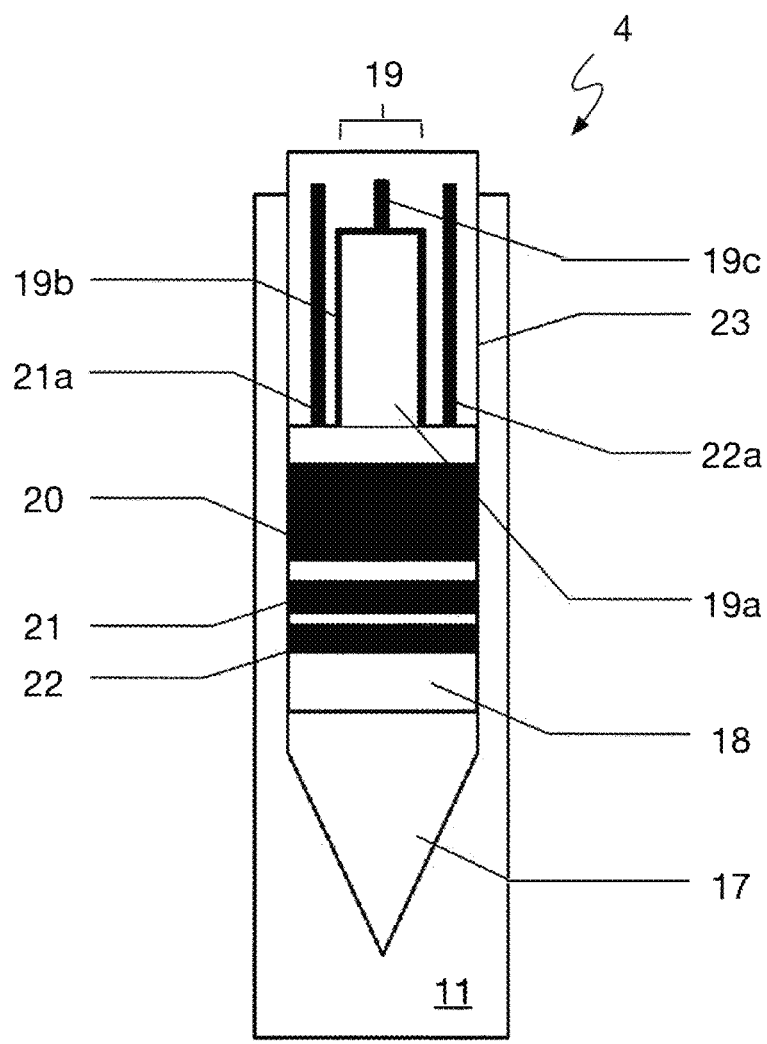
FIG. 4 schematically shows a potential measuring assembly, in particular a pH sensor assembly, for a sensor device according to an embodiment of the invention.

FIG. 4 shows a potential measuring assembly 4, in particular a pH sensor assembly, according to an embodiment of the invention which has been stabbed into a soil 11 to be analyzed and which may be provided in particular in a sensor device 1 according to FIG. 1 or FIG. 2. The potential measuring assembly 4 comprises a second support element 17 in the form of a spike, the shape of which may in particular substantially correspond to that of the first support element 12 of the impedance/temperature sensor assembly 3. A passivation layer 18, in particular a polymer passivation (e.g. of HDPE), is provided on a surface portion of the second support element 17, which surface portion is intended to come into contact with the soil 11 to be analyzed in the stabbed-in condition.

On this passivation layer 18, a metal oxide electrode 21 on the one hand, as well as a calibration electrode 22 are arranged in the form of annular conductive tracks, with the aid of which, if the electrical resistance of the soil 11 is known, which can be determined in particular by means of the impedance/temperature sensor assembly 3, a state, in particular a layer thickness, of the metal oxide electrode 21 can be determined by means of resistance measurement or conductivity measurement between the two electrodes 21 and 22, which are electrically coupled via the soil 11. The layer thickness can then be used as a calibration quantity for the actual measurement of an acidic or a basic character, in particular a pH value, of the soil 11. In particular, the measurement can be performed before each pH measurement, or cyclically at predetermined time intervals. In this way, the potential measuring assembly is able to carry out an (in situ) auto-calibration independently.

The metal oxide electrode 21, as well as the calibration electrode 22 are each electrically insulated, by the passivation layer 18, from the second support element 17, which may in particular be made of metal, and from each other. The calibration electrode 22 may in particular contain a conductive polymer material and/or a conductive composite material or be made entirely of them. The metal oxide electrode 21, as well as the calibration electrode 22 each comprise electrical contacts 21a and 22a, respectively, which may in particular be made of the same material as the associated electrode 21 and 22.

In order to measure the acidic or basic character of the soil by means of a potential measurement, the potential measuring assembly 4 further comprises an electrolyte/metal reference electrode 19 (for example AgCl/Ag electrode), which contains, as components arranged in a metal housing 23 (metal cap) constructed as part of, or as supplement of, the second support element 17, an electrolyte vessel 19b for receiving a liquid or paste-like electrolyte 19a as an electrolyte reference electrode, as well as a metal reference electrode 19c which is in electrically conductive contact with the electrolyte vessel 19b and the electrolyte 19a located therein. In particular, a robust mechanical protection of the reference electrode 19 is achieved by means of the metal housing 23.

The combination of the metal oxide electrode 21, the electrolyte/metal reference electrode 19, as well as an ion diaphragm 20 which is arranged therebetween on the surface of the second support element 17 and which is in ion-conducting contact with the electrolyte/metal reference electrode 19 and which can also be brought into ion-conducting contact with the metal oxide electrode via the surrounding soil 11 during the measurement process, represents a measuring device for measuring the acidic or basic character of the soil 11 on the basis of the chemical redox reaction already mentioned above:

$$x\text{Me} + y\text{H}_2\text{O} \leftrightarrow \text{Me}_x\text{O}_y + y2\text{H}^+ + y2e^-$$

the reaction equilibrium of which is, to a large degree, also determined by the concentration of hydrogen ions ($H^+$) present in the soil 11, so that the $H^+$ ion concentration in the soil and thus its pH value can be determined by means of the ion currents occurring during the measurement or the potential difference arising between the metal oxide electrode 21 and the electrolyte/metal reference electrode 19, taking into account a calibration which is based on the described measurement of the state of the metal oxide electrode 21.

Figure 5:
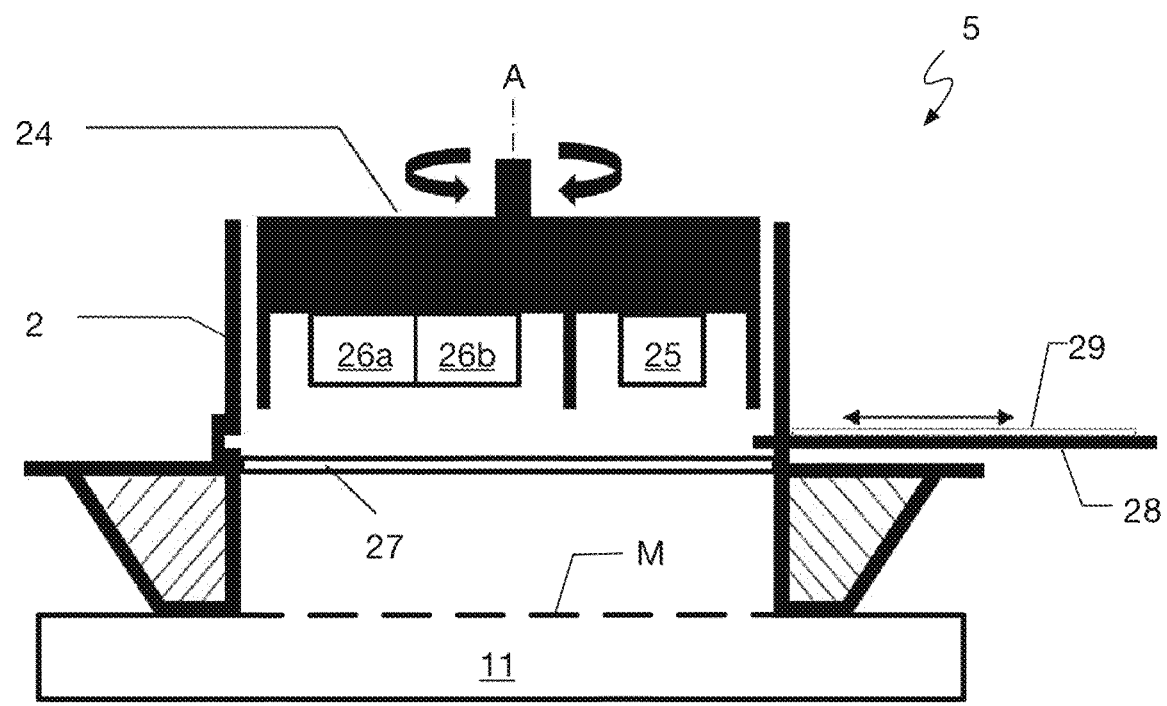
FIG. 5 schematically shows an absorption spectrometer assembly for a sensor device according to an embodiment of the invention.

FIG. 5 schematically shows an absorption spectrometer assembly 5 for a sensor device according to the invention, which in particular can be the sensor device 1 according to FIG. 1 or FIG. 2. In accordance with this, in the following, reference is again made to the sensor device 1. The absorption spectrometer assembly 5 comprises a substantially disk-shaped carrier 24 which is rotatable about an axis A and which is fitted into the housing 2 of the sensor device 1 between the two sensor assemblies 3 and 4, wherein one disk surface of the carrier 24 faces towards an opening of the housing 2, which opening serves as a measuring opening or measuring window of the absorption spectrometer assembly 5. The virtual area of this opening, which is located at its outer geometric boundary, can also be referred to as the measuring surface M, which in measurement operation typically comes to lie at least substantially parallel to the surface of the soil 11 to be analyzed, or which coincides with it, and which in FIG. 5 is shown as a dashed line. The carrier 24 is positioned with respect to this measuring surface M in such a way that it comes to lie above the surface of the soil during a measurement operation, whereby a minimum distance is defined by the shape of the housing 2. On the side of the carrier 24 which faces towards the measuring surface, two (or more) individual MEMS absorption spectrometers 26a, 26b are arranged on the carrier 24, each of which at least partially covers different spectral ranges and whereby they cumulatively cover a UV-VIS-NIR spectral range, which in particular includes the spectral range from 350 nm to 1700 nm. The use of MEMS technology to manufacture the absorption spectrometers makes the production of particularly small and thus space-efficient embodiments possible.

In addition, a source 25 for electromagnetic radiation is provided on the same side of carrier 24, for example a halogen lamp whose radiation covers this UV-VIS-NIR spectral range. The source 25 and the absorption spectrometers 26a, 26b are arranged with respect to each other, or optically separated from each other by a screen formed on the carrier 24, in such a way that the radiation of the source 25 can only reach the absorption spectrometers 26a, 26b in an indirect manner in the form of reflected radiation.

In addition, the absorption spectrometer assembly 5 comprises a protective optical system 27, which can be constructed in particular in the form of a disc consisting of a scratch-resistant material that is at least largely transparent in the spectral range mentioned, for example a sapphire glass disc, with a hydrophilic nanocoating that improves scratch protection. The nanocoating makes it easier to keep the optical system clean and it also means it easier to clean it and it increases the mechanical robustness of the optical system. The protective optical system 27 is located between the carrier 24 with the optical components 25, 26a, 26b located thereupon, and the measuring surface (at a distance of e.g. approx. 3 cm from it), which can protect the optical components against harmful external influences, in particular from the soil 11 to be analyzed, such as dust and moisture as well as damage caused mechanically.

Further, the absorption spectrometer assembly 5 comprises a closing or shutter device 28, which is essentially a disc-shaped screen which can be extended (and retracted again), preferably parallel to the protective optical system 27, into the space defined between the carrier 24 with the optical components 25, 26a, 26b and the protective optical system 27. On its side facing towards the optical components 25, 26a, 26b, this screen is coated with a calibration coating 29, for example Spectralon. Spectralon is a material made of sintered PTFE which has an extremely high and uniform reflectance in the ultraviolet (UV) and in the visible (VIS) ranges, as well as in the near infrared (NIR) range of the electromagnetic spectrum. It exhibits Lambertian reflection behavior, i.e. it reflects very diffusely or matt. The calibration coating 29 serves as a calibration reference with the aid of which the absorption spectrometers 26a, 26b can be calibrated in situ when, for this purpose, the screen has been extended into the space between the absorption spectrometers 26a, 26b and the protective optical system 27. During the measurement process for soil analysis, however, the screen is retracted so as not to disturb the beam path between the optical components 25, 26a, 26b and the soil 11.

In addition, the absorption spectrometer assembly 5 is configured in such a way that during measurement operation, when the soil surface of the soil 11 to be analyzed, at least substantially, coincides with the measuring surface, the carrier 24 is rotated about the axis of rotation A, which is then substantially perpendicular to the measuring surface, while the source 25 and the two absorption spectrometers 26a, 26b are activated in order to record an absorption spectrum at the absorption spectrometers 26a, 26b in the spectral range mentioned, on the basis of the radiation of the source 25 reflected at the soil surface.

Figure 6:
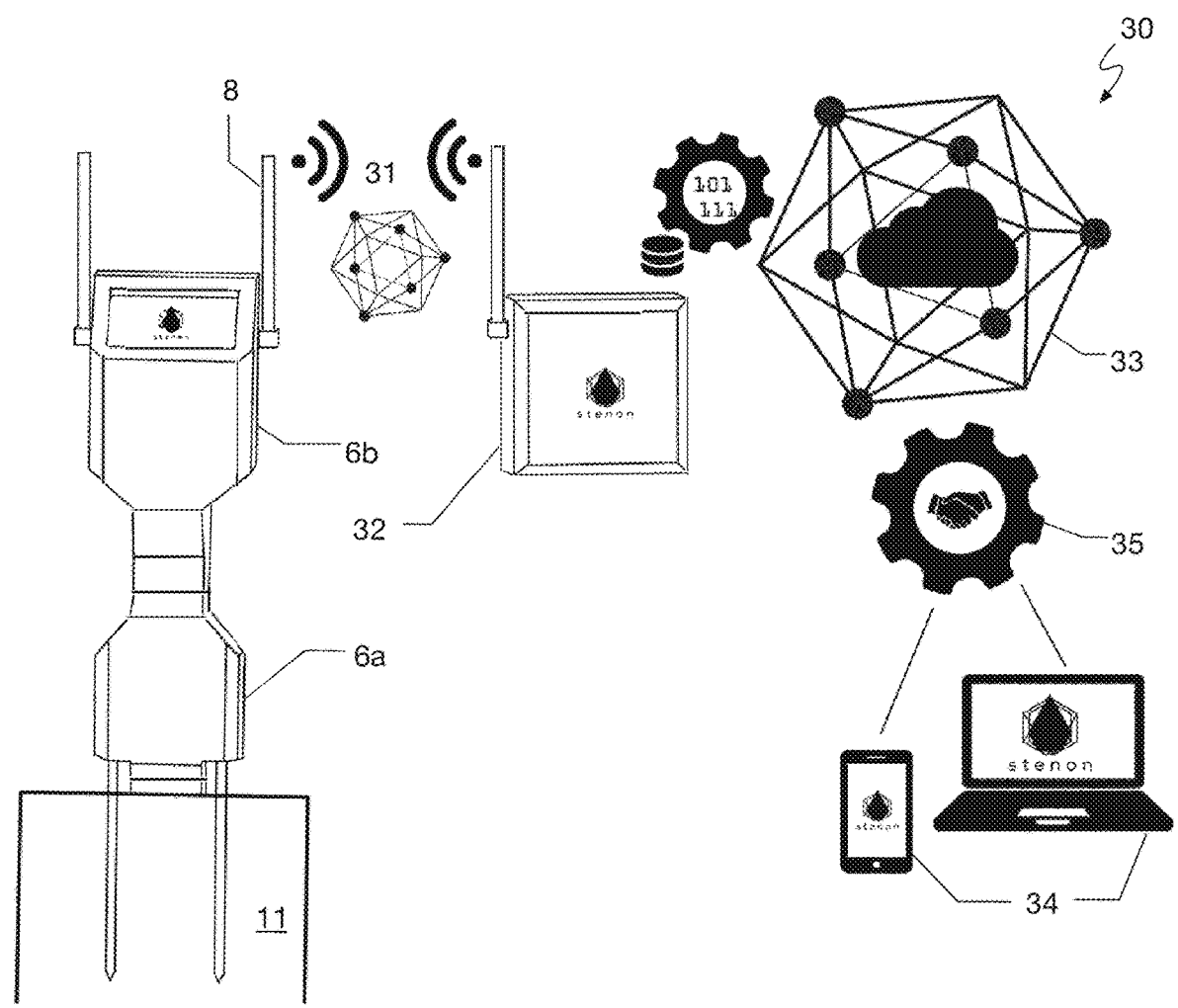
FIG. 6 shows a schematic overview of an overall system for soil analysis, according to an embodiment of the invention.

FIG. 6 shows a schematic overview of an (overall) system 30 for soil analysis, according to an embodiment of the invention. The system 30 comprises one, or typically several, sensor devices, in particular sensor devices 1 according to FIG. 1 or 2 (of which only one is shown here) which serve to obtain on site, i.e. in situ, measurement data which characterize properties of a soil to be analyzed. These measurement data can then be transmitted from the respective sensor device 1 by means of the communication device 8 via a communication link, which can be constructed in particular as a block chain transfer, to a device-external counterpart 33, which can be implemented in particular in the form of one or more network nodes (for example servers) in a computer network or in a cloud environment.

In the example shown, the transmission takes place in several stages, in that the measurement data as well as, if applicable, any associated metadata for the measurement are first transmitted via a wireless communication link, which can be implemented in particular by means of LoRa or NB-IoT radio technologies, to a gateway 32, which can be located, for example, on the farm of a farmer using the system 30. From this gateway 32, the measurement data and the metadata can be further transmitted to the counterpart 33 for evaluation, for example in the classical way via a wireless or a wired Internet connection. It is envisaged that preferably a block chain transfer is used again, so that the entire communication between the sensor device 1 and the counterpart 33 is implemented by means of block chain technology. This communication path is bidirectional, so that it can also be used in the opposite direction, in particular for the transmission, to the respective sensor device 1, of analysis data obtained by the counterpart 33 on the basis of the measurement data and meta data transmitted to it. Depending on the particular embodiment, the meta data acquired by the respective sensor device 1 can contain, in particular, information regarding the point in time and the location of a soil measurement carried out, as well as a unique device identification and/or user identification.

In addition, or as an alternative, a further communication link 35 can be provided between the counterpart 33 and one or more user terminal devices 34, which further communication link 35 can be constructed in particular as remote access, for example via a web portal, and can again advantageously be implemented by means of block chain technology. All communication links in the system are preferably encrypted for the purpose of maintaining data security and to protect against manipulation, for example by means of known asymmetric or symmetric encryption methods. Communication link 35 offers a further way of accessing the analysis data obtained. For example, the farmer or horticulturist can access the analysis data in this way even a relatively large period of time after the measurement was carried out, for example from his farm or even while on the move, via a corresponding terminal device 34, without having to have the sensor device 1 with him.

Figure 7:
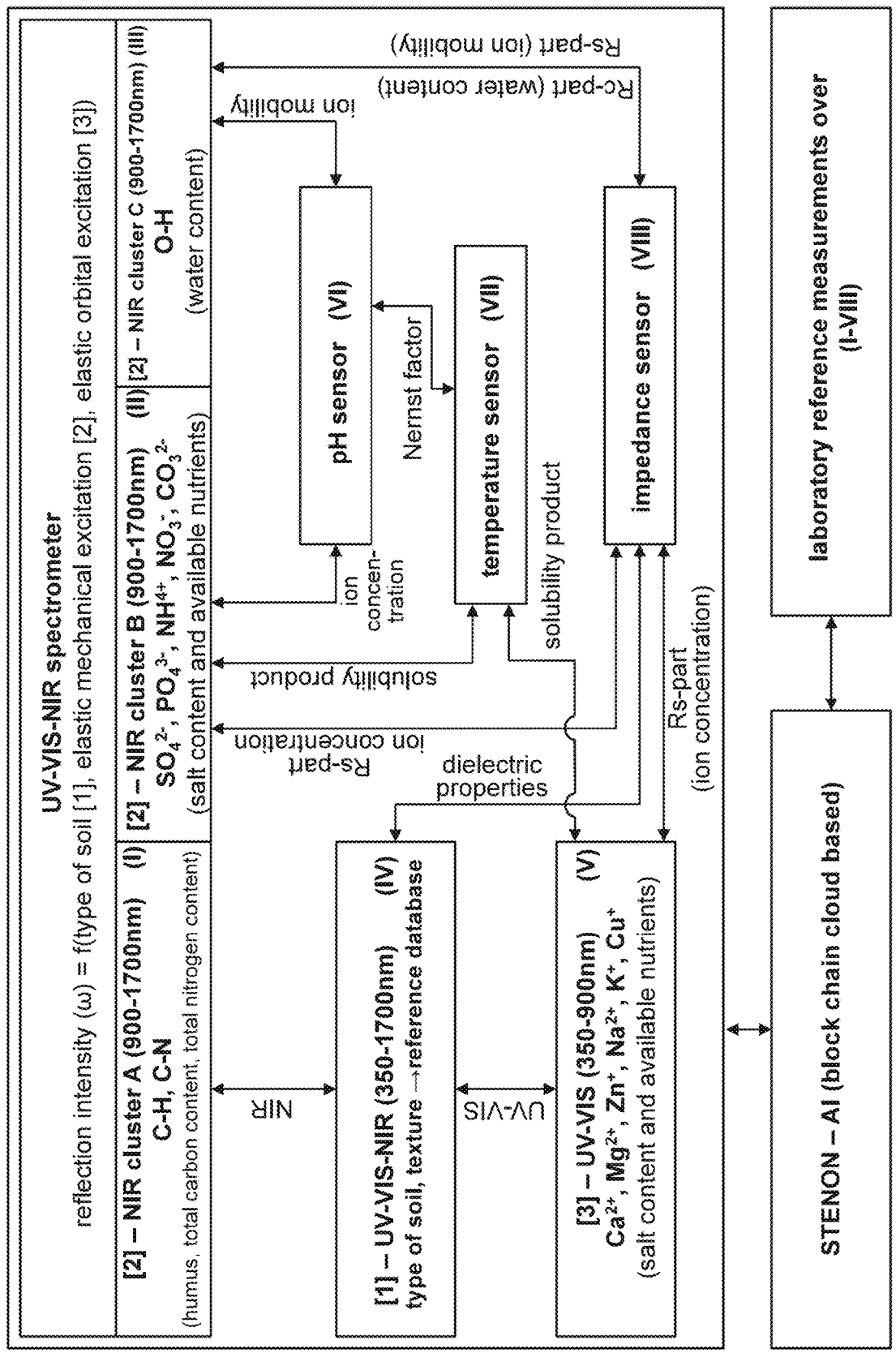
FIG. 7 shows an overview, by way of example, of various correlations between individual measurands which can be detected by the sensors of the sensor device according to FIG. 1 or 2, and by means of which various soil properties can be determined within the scope of a data fusion according to the method according to the invention.

FIG. 7 shows an overview, by way of example, of various correlations between individual measurands which can be detected by the sensors of the sensor device according to FIG. 1 or 2, and by means of which various soil properties can be determined within the scope of a data fusion (or here synonymously: sensor fusion) according to the method according to the invention. The correlations are marked by means of corresponding, labeled arrows, whereby the labels indicate those physical or chemical quantities which can be used within the scope of the data fusion in particular to form correlations between the various measurement quantities directly produced by the sensor assemblies 3 to 5, which enable additional, derived soil properties to be determined and/or which enable the accuracy of the achievable results to be increased. In particular, a number of important parameters for agriculture and horticulture can be determined in this way, which includes in particular the total nitrogen content, the total humus content, the ratio of nitrogen to organic matter, the amount of available phosphate, the amount of available potassium, the amount of available magnesium, the electrical conductivity, the moisture of the soil and the pH value of the soil.

While at least one example embodiment has been described above, it is to be noted that there are a large number of variations to this. It is also to be noted that the example embodiments which have been described only represent non-limiting examples, and that it is not intended to thereby limit the scope, the applicability or the configuration of the devices and methods described here. Rather, the preceding description will provide the skilled person with instructions for the implementation of at least one example embodiment, whereby it is understood that various changes can be made, as regards the functionality and the arrangement of the elements described in an example embodiment, without deviating from the subject matter respectively defined in the appended claims, as well as its legal equivalents.

LIST OF REFERENCE SIGNS

1 Sensor device
2 Housing
3 Impedance/temperature sensor assembly
4 Potential measuring assembly, in particular pH sensor assembly
5 Absorption spectrometer assembly
6a Sensor module
6b Operating/radio module
7 Position determination device
8 Communication device
9 Man-machine interface, in particular operating display
10 Carrying handle or manipulating handle
11 soil
12 (first) support element, in the shape of a spike
13 Passivation, in particular polymer passivation, of the first support element
14 conductive tracks
14a first conductive track
14b second conductive track
15 integrated PCB with control device and temperature sensor
15a Control device
15b Signal preamplifier
15c temperature sensor
16 Metal housing, in particular metal cap, of the first support element
17 (second) support element, in the shape of a spike
18 Passivation, in particular polymer passivation, of the second support element
19 Electrolyte/metal reference electrode
19a Electrolyte reference electrode (electrolyte)
19b Electrolyte vessel
19c metal reference electrode
20 Ion diaphragm
21 Metal oxide electrode
21a Contact of the metal oxide electrode
22 Calibration electrode
22a Contact of the calibration electrode
23 Metal housing, in particular metal cap, of the second support element
24 rotatable carrier with axis of rotation A
25 Electromagnetic radiation source
26a, b MEMS absorption spectrometer with measuring surface M
27 (protective) optical system, in particular sapphire glass with hydrophilic nanocoating
28 Shutter device
29 Calibration reference, in particular calibration coating
30 System for in situ soil analysis
31 Communication link, in particular block chain transfer
32 Gateway
33 counterpart, in particular block chain/cloud environment or local evaluation device
34 User terminal device
35 Remote access

The invention claimed is:

1. A sensor device (1) for in situ soil analysis, comprising:
a sensor assembly with one or more sensors which are configured individually or cumulatively for simultaneous in situ measurement of at least two of the following soil properties of a soil (11) to be analyzed and for providing corresponding respective measurement data:
(a) impedance spectrum
(b) temperature; and
(c) absorption spectrum in a spectral range which extends from NIR to UV, NIR-VIS-UV
wherein;
the distance between each two sensors of the sensor assembly, defined in relation to their respective measurand transducers, does not exceed a value of 10 cm
in order to measure, in situ, the impedance spectrum $(Z(\omega))$, the sensor assembly is configured to measure an alternating current resistance of a portion of soil to be measured, as a function of the frequency ($\omega$) of an alternating measuring voltage which is applied to the portion of soil.

2. The sensor device (1) according to claim 1, wherein the sensor assembly further comprises one or more sensors which are configured individually or cumulatively to carry out, simultaneously with the other measurements, and in situ measurement of an acidic or a basic character of the soil (11) to be analyzed, and to provide corresponding measurement data.

3. The sensor device (1) according to claim 2, wherein the first support element is electrically conductive, at least in an area which is covered by the conductive tracks (14), and the control device (15a) is further configured to apply a ground potential to this at least one area during the detection of the impedance spectrum of the soil (11) to be analyzed.

4. The sensor device (1) according to claim 2, wherein the predetermined frequency range includes the range from 100 Hz to 1 MHz.

5. The sensor device (1) according to claim 2, wherein:
the first support element is constructed as a spike which, at least in part, is hollow, for at least partial introduction into the soil (11) to be analyzed,
wherein an insulation layer is applied to the surface of the spike, and on which, in turn, the two conductive tracks (14) are arranged; and
the control device (15a) is located in the interior of a hollow portion of the first support element (12).

6. The sensor device (1) according to claim 2, wherein the sensor assembly comprises a temperature sensor (15c) for detecting a temperature of the soil (11) to be analyzed, wherein this, together with the impedance sensor, is constructed as an integrated impedance/temperature sensor assembly (3), which is configured to detect, simultaneously and in situ, an impedance spectrum as well as a temperature of the soil (11) to be analyzed and to make this available respectively in the form of corresponding measurement data.

7. The sensor device (1) according to claim 1, wherein the sensor assembly comprises an absorption spectrometer assembly (5) for in situ detection of an absorption spectrum of the soil (11) to be analyzed, comprising:
at least two MEMS absorption spectrometers (26a, 26b), the spectral coverage of which differs at least for some portions of the electromagnetic spectrum, so that an absorption spectrum of the soil (11) to be analyzed can be detected cumulatively by the entirety of the MEMS absorption spectrometers (26a, 26b), which absorption spectrum has portions in the NIR range as well as in the VIS range and also in the UV range.

8. The sensor device (1) according to claim 7, wherein the absorption spectrometer assembly (5) further comprises a movable carrier (4) on which the absorption spectrometers are arranged in such a way that, when the carrier (24) is moved relative to a virtual measuring surface on which the soil (11) to be analyzed comes to rest during the measurement operation of the sensor device (1), they can spectrometrically measure an area of the soil (11) to be scanned by the absorption spectrometers in order to detect an absorption spectrum which is integrated over the area to be scanned.

9. The sensor device (1) according to claim 7, wherein the absorption spectrometer assembly (5) further comprises a movable shutter device (28) which is configured to temporarily move a screen into a space defined between the absorption spectrometers and the measuring surface, wherein a calibration reference (29) is arranged on the side of the screen which faces towards the absorption spectrometers, for the calibration of at least one of the absorption spectrometers.

10. The sensor device (1) according to claim 7, wherein the absorption spectrometer assembly (5) further comprises an optical system (27) which, in a wavelength range corresponding to the absorption spectrum to be detected, is at least substantially optically transparent, which optical system (27) is arranged in the space between the absorption spectrometers and the measuring surface, in order to spatially separate these from each other;
wherein, on its side facing towards the measuring surface, the optical system (27) is provided with a hydrophilic nanocoating which improves the scratch protection.

11. The sensor device (1) according to claim 1, wherein the sensor assembly comprises a potential measuring assembly (4) for in situ detection of an acidic or basic character of the soil (11) to be analyzed, comprising:
a second support element (17);
an electrolyte/metal reference electrode (19) which is arranged in or on the second support element;
a metal oxide electrode (21) which is arranged on a surface of the second support element (17), which surface is intended to contact the soil (11) to be analyzed during a measurement operation;
an ion diaphragm (20) which is arranged on the second support element between the metal oxide electrode (21) and the electrolyte/metal reference electrode (19) and which is in contact with the electrolyte/metal reference electrode (19);
a corrosion resistant calibration electrode (22) which is arranged on the surface of the second support element (17) provided for contacting the soil (11) to be analyzed and which corrosion resistant calibration electrode (22) is electrically insulated from the metal oxide electrode (21); and
a measuring device which is configured:
in order to determine a current state of the metal oxide electrode (21), to measure an electrical resistance arising between the calibration electrode (22) and the metal oxide electrode (21) and/or to measure an electrical capacitance arising therebetween when these two electrodes are each in contact with the soil (11) to be analyzed; and
in order to determine an acidic or a basic character of the soil (11) to be analyzed, to measure an electric potential difference arising between the reference electrode and the metal oxide electrode (21), taking into account a measurement calibration previously determined on the basis of the determined current state of the metal oxide electrode (21), when these two electrodes are each in contact with the soil (11) to be analyzed.

12. The sensor device (1) according to claim 11, wherein the calibration electrode (22) is made of a material that contains an electrically conductive and corrosion resistant polymer or composite material.

13. The sensor device (1) according to claim 11, wherein the second support element is constructed as a spike for at least partial introduction into the soil (11) to be analyzed, wherein an insulating layer is applied to the surface of the spike, on which insulating layer the metal oxide electrode (21), the ion diaphragm (20) and/or the calibration electrode (22) are arranged.

14. The sensor device (1) according to claim 1, further comprising a communication device (8) for the transmission of detected measurement data to a counterpart which is external with respect to the sensor device (1), for evaluation.

15. The sensor device (1) according to claim 14, wherein the communication device (8) is configured to transmit the measurement data wirelessly by means of communication on the basis of LoRa radio technology and/or NarrowBand Internet of Things, NB-IoT, radio technology.

16. The sensor device (1) according to claim 14, further comprising a secure storage device for storing, protected against unauthorized access, a unique device identification of the sensor device (1) and/or at least a cryptographic key for encrypting measurement data and/or metadata transmitted by means of the communication device (8).

17. The sensor device (1) according to claim 14, wherein the communication device (8) is further configured to write, into a block chain acting as an external counterpart, measurement data and/or metadata to be transmitted, or to cause another external counterpart to write, into a block chain, the measurement data and/or metadata transmitted to it.

18. The sensor device (1) according to claim 17, wherein the sensor device (1) is configured to carry out an authentication of a user of the sensor device (1) and to allow the transmission of measurement data and/or metadata to an external counterpart only if the authentication has been successful.

19. The sensor device (1) according to claim 1, further comprising a position determination device (7) for determining a current position of the sensor device (1) and to provide corresponding metadata characterizing the position.

20. The sensor device (1) according to claim 1, wherein the impedance sensor assembly includes an impedance sensor for in situ detection of an impedance spectrum of the soil (11) to be analyzed, wherein the impedance sensor comprises:
a first support element (12);
two conductive tracks (14) which are arranged on the first support element (12) but which are electrically insulated from this and from each other, at least one of which contains an electrically conductive, corrosion resistant polymer or composite material;
a control device (15a), which is configured to apply an AC voltage between the two conductive tracks (14), to vary its frequency over a predetermined frequency range, and during the course of this, during operation of the sensor device (1), when this is introduced into the soil (11) to be analyzed in such a way that the conductive tracks (14) are in electrical contact with the soil (11) to be analyzed, to detect an impedance spectrum of the soil (11) to be analyzed in response to the AC voltage applied to it via the conductive tracks (14) and to provide the impedance spectrum in the form of corresponding measurement data.

21. A method for soil analysis, comprising:
receiving measurement data relating to at least two of the following soil properties of a soil (11) to be analyzed:
(a) impedance spectrum ($Z(\omega)$), which indicates the alternating current resistance of a portion of soil to be measured, as a function of the frequency (ω) of an alternating measuring voltage which is applied to the portion of soil;

(b) temperature (c) absorption spectrum in a spectral range which extends from NIR to UV, NIR-VIS-UV determining at least one of the soil properties or at least one soil property derived therefrom on the basis of a combination of the received measurement data by means of data fusion in order to obtain a respective measurement result for the at least one soil property to be determined.

22. The method according to claim 21, wherein the measurement data are detected by a sensor device (1).

23. The method according to claim 21, wherein the method is carried out in at least one central node (33) of a network, which at least one central node (33), in order to receive the respective measurement data, is configured to be in communication connection (31) with a plurality of sensor devices (1) for detecting the respective measurement data.

24. A computer program which is configured, when it is run on a processor platform, to carry out the method according to claim 21.

25. A device (33) for soil analysis, wherein the device is arranged to carry out the method according to claim 21.

26. The device (1, 33) according to claim 25, comprising a sensor device (1) according to claim 1 for detecting the measurement data.

27. The method according to claim 22, further comprising:

receiving measurement data relating to the following soil property of the soil (11) to be analyzed: acidic or basic character.

* * * * *